United States Patent [19]

Warriner

[11] Plant 4,850

[45] May 25, 1982

[54] ROSE PLANT 71-12673

[75] Inventor: William A. Warriner, Tustin, Calif.

[73] Assignee: Jackson & Perkins Company, Medford, Oreg.

[21] Appl. No.: 190,091

[22] Filed: Sep. 23, 1980

[51] Int. Cl.[3] ..... A01H 5/00

[52] U.S. Cl. ..... Plt./19

[58] Field of Search ..... Plt./19–20

*Primary Examiner*—Robert E. Bagwill

*Attorney, Agent, or Firm*—Klarquist, Sparkman, Campbell, Leigh, Whinston & Dellett

[57] ABSTRACT

A hybrid tea rose variety having red flowers borne on long length stems of a very vigorous plant, open flowers having a very slight fragrance.

1 Drawing Figure

This present invention relates to a new and distinct variety of rose plant of the hybrid tea class which was originated by me by crossing an unnamed variety with an unnamed variety.

The primary objective of this breeding was to produce a new rose variety of vigorous growth, abundant blooms in a red or near red color. This objective was substantially achieved along with other desirable improvements as evidenced by the following unique combination of characteristics which are outstanding in the new variety and which distinguish it from its parents as well as from all other varieties of which I am aware:

1. A very vigorous plant reaching 6′ to 6½′ at Irvine, Calif.
2. Pointed buds of red hue.
3. Large flowers opening well in cool spring weather as well as summer weather.
4. Open flower color a cerise red shown in the Royal Horticultural Society Colour chart as Red 53B.
5. Very slight fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with the Royal Horticultural Society Colour Chart except where ordinary dictionary significance of color is indicated.

Parentage:

*Seed parent.*—Unnamed variety.

*Pollen parent.*—Unnamed variety.

Classification:

*Botanical.*—Rose hybrid.

*Commerical.*—Hybrid tea.

FLOWER

Observations made from specimens grown at Irvine, Calif., in August, 1980.

Blooming habit: Continuous.

Bud:

*Size.*—1″ to 1⅛″ when petals start to unfurl.

*Form.*—Pointed ovoid.

*Color.*—When sepals first unfold, Red 53B; when half blown, upper side of petals Red 53C, lower side of petals Red 54B to 54C.

*Sepals.*—Color: Outer surface Green 138A. Surface has numerous stipitate glands. Three appendaged sepals lightly appendaged; two unappendaged sepals hairy edged.

*Receptacle.*—Color: Green 138A. Shape: Funnel. Size: Broad, small. Surface: Smooth.

*Peduncle.*—Length: Short. Surface: Prickly and glandular. Color: Light Green. Strength: Stiff, erect.

*Opening.*—Spiral.

Bloom:

*Size.*—Large. Average open size is 4½″.

*Borne.*—Singly or several together.

*Stems.*—Long, strong.

*Form.*—When first open, high center. Permanence: Outer petal edges slightly curled.

*Petalage.*—Number of petals under normal conditions, 25 to 30.

*Color.*—Center of flower: Upper side of petals Red 53C; reverse side of petals Red 53D; base of petals sharply defined ¼″ of yellow 3A. General tonality from a distance Red 53B.

*Variegations.*—None.

*Discoloration.*—General tonality on third day: Slight fading to 53D or slightly lighter.

*Fragrance.*—Slight.

Petals:

*Texture.*—Thin.

*Shape.*—Round, often broader than long.

*Form.*—Edges slightly quilled.

*Arrangement.*—Irregular. Petaloids in center, few.

*Persistence.*—Drop off cleanly.

*Lastingness.*—On the plant, long. As cut flower, long.

Reproductive parts:

*Anthers.*—Large, many. Color: Yellow. Arrangement: Regular around styles.

*Filaments.*—Color: Yellow.

*Pollen.*—Gold yellow.

*Styles.*—Color: Pale green basal half, reddish upper half.

*Stigmas.*—Color: Yellow.

PLANT

Form: Bush.
Growth: Very vigorous, upright.
Foliage: Number of leaflets on normal mid-stem leaves, 5.
*Size.*—Medium.
*Quantity.*—Normal.
*Color.*—New foliage: Red Purple 59A. Old foliage: Green 139A.
Leaflets:
*Shape.*—Oval.
*Texture.*—Upper side: Leathery.
*Edge.*—Serrated.
*Serration.*—Single, small.
*Petiole.*—Rachis: Color: Reddish. Underside: Prickles.
*Stipules.*—Long and narrow, bearded.
*Disease resistance.*—Mildly susceptible to blackspot under normal growing conditions at Irvine, Calif.

Wood:
*New wood.*—Color: Light green. Bark: Smooth.
*Old wood.*—Color: Green. Bark: Smooth.
Prickles:
*Quantity.*—On main stalks from base, many. On laterals from stalk, many.
*Form.*—Long base, hooked downward.
*Color when young.*—Green and red.
*Position.*—Irregular.
Small prickles:
*Quantity.*—On main stalks, few. On laterals, few.
*Color.*—Brown.

I claim:

1. A new and distinct variety of rose plant of the hybrid tea class, substantially as herein shown and described, characterized particularly as to novelty by the unique combination of its vigorous growth, abundant blooms, cerise red flower color and very slight fragrance.

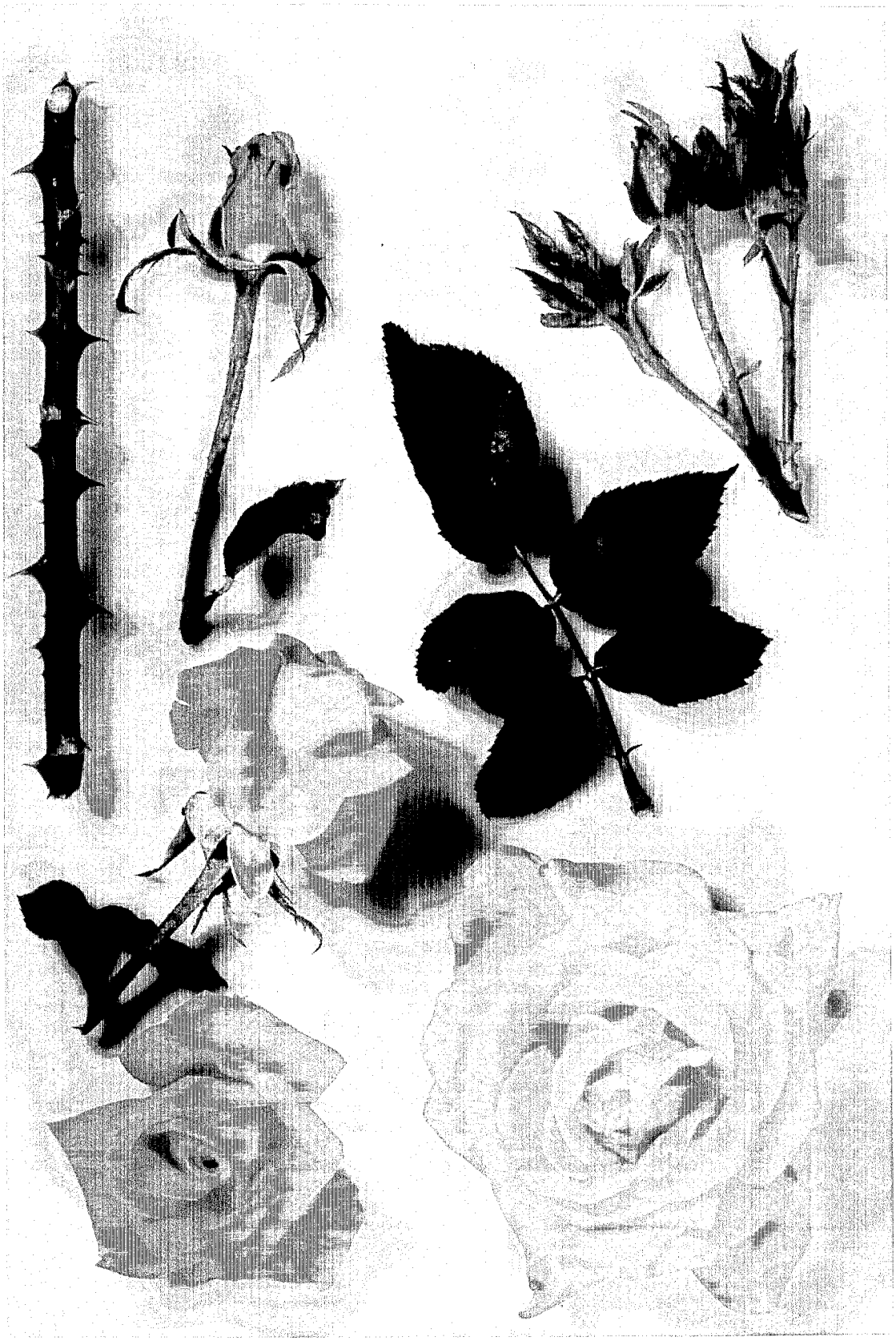

* * * * *